(12) United States Patent
Ishihara et al.

(10) Patent No.: US 9,206,107 B2
(45) Date of Patent: Dec. 8, 2015

(54) METHOD FOR PRODUCING CARBOXYLIC ACID AND ALCOHOL BY HYDROLYSIS OF ESTER

(71) Applicant: NATIONAL UNIVERSITY CORPORATION NAGOYA UNIVERSITY, Nagoya-shi, Aichi (JP)

(72) Inventors: Kazuaki Ishihara, Nagoya (JP); Akira Sakakura, Nagoya (JP); Yoshiki Koshikari, Nagoya (JP)

(73) Assignee: NATIONAL UNIVERSITY CORPORATION NAGOYA UNIVERSITY, Nagoya-shi (JP)

( * ) Notice: Subject to any disclaimer, the term of this patent is extended or adjusted under 35 U.S.C. 154(b) by 0 days.

(21) Appl. No.: 14/369,613

(22) PCT Filed: Dec. 13, 2012

(86) PCT No.: PCT/JP2012/082310
§ 371 (c)(1),
(2) Date: Jun. 27, 2014

(87) PCT Pub. No.: WO2013/099623
PCT Pub. Date: Jul. 4, 2013

(65) Prior Publication Data
US 2014/0378692 A1 Dec. 25, 2014

(30) Foreign Application Priority Data
Dec. 28, 2011 (JP) .................... 2011-289040

(51) Int. Cl.
| | | |
|---|---|---|
| C07C 51/09 | (2006.01) |
| C07C 29/09 | (2006.01) |
| B01J 31/02 | (2006.01) |
| C07C 29/147 | (2006.01) |
| C07C 211/55 | (2006.01) |

(52) U.S. Cl.
CPC ............. *C07C 51/09* (2013.01); *B01J 31/0215* (2013.01); *B01J 31/0239* (2013.01); *B01J 31/0268* (2013.01); *B01J 31/0271* (2013.01); *C07C 29/095* (2013.01); *C07C 29/147* (2013.01); *C07C 211/55* (2013.01); *B01J 2231/40* (2013.01)

(58) Field of Classification Search
None
See application file for complete search history.

(56) References Cited

FOREIGN PATENT DOCUMENTS

| | | | |
|---|---|---|---|
| GB | 1076964 | * 7/1967 | ............ C08G 33/00 |
| JP | A-2003-64023 | 3/2003 | |
| JP | A-2004-26723 | 1/2004 | |
| JP | A-2004-358301 | 12/2004 | |
| JP | A-2010-209027 | 9/2010 | |
| JP | A-2010-235505 | 10/2010 | |

OTHER PUBLICATIONS

Sakakura et al., "Hydrophobic N,N-Diarylammonium Pyrosulfates as Dehydrative Condensation Catalysts under Aqueous Conditions," *Organic Letters*, 2012, vol. 14, No. 1, pp. 30-33.
Koshikari et al., "N,N-Diarylammonium Pyrosulfate as a Highly Effective Reverse Micelle-Type Catalyst for Hydrolysis of Esters," *Organic Letters*, 2012, vol. 14, No. 12, pp. 3194-3197.
Manabe et al., "Dehydration Reactions in Water, Surfactant-Type Brønsted Acid-Catalyzed Direct Esterification of Carboxylic Acids with Alcohols in an Emulsion System," *Journal of the American Chemical Society*, 2001, vol. 123, pp. 10101-10102.
Manabe et al., "Dehydration Reactions in Water. Brønsted Acid—Surfactant-Combined Catalyst for Ester, Ether, Thioether, and Dithioacetal Formation in Water," *Journal of the American Chemical Society*, 2002, vol. 124, pp. 11971-11978.
International Search Report issued in International Patent Application No. PCT/JP2012/082310 mailed Feb. 12, 2013.
Bhattacharya et al., "Metallomicelles as Potent Catalysts for the Ester Hydrolysis Reactions in Water," Coordination Chemistry Reviews, vol. 253, pp. 2133-2149, 2009.
Jul. 7, 2015 Supplementary Euroepan Search Report issued in European Application No. 12862745.2.

* cited by examiner

*Primary Examiner* — Yate K Cutliff
(74) *Attorney, Agent, or Firm* — Oliff PLC

(57) ABSTRACT

As shown by the following formula (1), after methyl laurate (2 mmol) and water (8 mL) are added to an ammonium pyrosulfate catalyst (5 mol %), a hydrolysis reaction of methyl laurate is carried out by heating for 24 hours at 60° C. while stirring is performed, so that lauric acid can be obtained with a yield of 86%.

[Chem. 1]

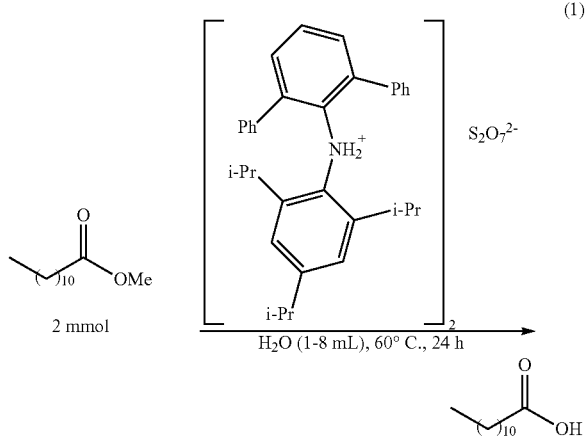

4 Claims, No Drawings

METHOD FOR PRODUCING CARBOXYLIC ACID AND ALCOHOL BY HYDROLYSIS OF ESTER

TECHNICAL FIELD

The present invention relates to a method for producing a carboxylic acid and an alcohol by hydrolysis of a carboxylic acid ester. In addition, the present invention relates to a catalyst used for the above production method.

BACKGROUND ART

A reaction to obtain a carboxylic acid and an alcohol by hydrolysis of a carboxylic acid ester is a fundamental reaction of synthetic processes for medicines, organic materials, and the like, and development of a highly efficient hydrolysis method has been strongly desired. Heretofore, hydrolysis of a carboxylic acid ester has been carried out using a stoichiometric amount or more of a base (such as lithium hydroxide, sodium hydroxide, or the like) in a homogeneous mixed solvent containing water and an organic solvent (methanol, THF, or the like). On the other hand, although not being a hydrolysis reaction of a carboxylic acid ester, a method for producing an ester compound by dehydration condensation of a carboxylic acid and an alcohol in the presence of sulfuric acid and a bully N,N-diarylamine has been developed by the present inventors as disclosed in Patent Literature 1.

CITATION LIST

Patent Literature

PTL 1: Japanese Unexamined Patent Application Publication No. 2010-209027

SUMMARY OF INVENTION

Technical Problem

In the above related hydrolysis method, in order to homogeneously mix water and a substrate, the use of an organic solvent is indispensable, and a heterogeneous system is formed unless an organic solvent is used, so that the reactivity of hydrolysis may be degraded in some cases. However, the use of organic solvents has been an environmental issue for years, and in view of waste liquid treatment, it has also been desired to avoid the use of organic solvents. In addition, the cost of organic solvents is high as compared to that of water. Furthermore, in the above hydrolysis method, the base is neutralized by a carboxylic acid which is a reaction product. Hence, a stoichiometric amount or more of the base is inevitably used. In addition, disadvantageously, the above hydrolysis method may not be applied to a carboxylic acid ester which is unstable under a basic condition.

In order to solve the above problems, the present invention provides a method capable of producing a carboxylic acid and an alcohol by hydrolysis of a carboxylic acid ester even under conditions in which water is only used as a reaction solvent and a base is not used. In addition, the present invention also provides a catalyst used for the above production method.

Solution to Problem

The present inventors found out that when a newly developed Broensted acid catalyst is used a carboxylic acid and an alcohol can be obtained by efficient hydrolysis of a carboxylic acid ester in an aqueous solvent without using an organic solvent and a base, and hence the present invention was made.

A method for producing a carboxylic acid and an alcohol of the present invention is the method comprises hydrolyzing a carboxylic acid ester in water in the presence of an ammonium pyrosulfate catalyst represented by the following general formula (1)

[Chem. 1]

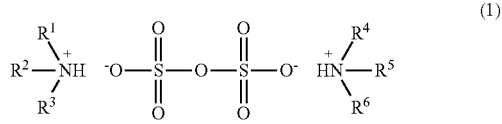

(1)

(in the formula, $R^1$ and $R^4$ each independently represent an aryl group, and $R^2$, $R^3$, $R^5$, and $R^6$ each independently represent an aryl group, an alkyl group, an alkenyl group, an alkynyl group, a cycloalkyl group, or a hydrogen atom).

In addition, a catalyst used for production of a carboxylic acid and an alcohol of the present invention is a catalyst which is used for producing a carboxylic acid and an alcohol by hydrolyzing a carboxylic acid ester into a carboxylic acid and an alcohol and which is formed of an ammonium pyrosulfate represented by the following general formula (3).

[Chem. 2]

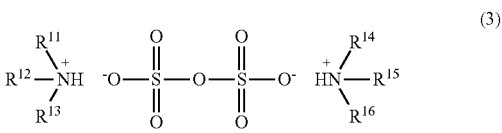

(3)

(In the formula, $R^{11}$ and $R^{14}$ each independently represent an aryl group, $R^{12}$, $R^{13}$, $R^{15}$, and $R^{16}$ each independently represent an aryl group, an alkyl group, an alkenyl group, an alkynyl group, a cycloalkyl group, or hydrogen atom.)

Advantageous Effects of Invention

According to the method for producing a carboxylic acid and an alcohol of the present invention, in the hydrolysis of a carboxylic acid ester, by the use of a new ammonium pyrosulfate as a catalyst, hydrolysis of a carboxylic acid ester efficiently progresses even in an aqueous solvent, and hence, a carboxylic acid and an alcohol can be obtained with a high yield. Hence, the use of an organic solvent and a base is not required. In addition, according to the catalyst used for producing a carboxylic acid and an alcohol of the present invention, hydrolysis activity of a carboxylic acid ester is excellent. Accordingly, a carboxylic acid ester can be hydrolyzed in an aqueous solvent without using an organic solvent and a base, and hence a carboxylic acid and an alcohol can be efficiently produced.

DESCRIPTION OF EMBODIMENTS

In a method for producing a carboxylic acid and an alcohol of the present invention, a usable carboxylic acid ester is a carboxylic acid ester represented by the following general formula (5)

[Chem. 3]

(5)

(in the formula, R' and R" each independently represent a monovalent hydrocarbon group) and is not particularly limited.

In the formula described above, as the monovalent hydrocarbon group, for example, an alkyl group, an alkenyl group, an alkynyl group, an aryl group, and a cycloalkyl group may be mentioned. As the alkyl group, a linear or a branched alkyl group may be mentioned and is not particularly limited. For example, as the linear alkyl group, a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, or an icosyl group may be mentioned. As the branched alkyl group, for example, an isopropyl group, an isobutyl group, a sec-butyl group, a tert-butyl group, a 2-methyl-1-butyl group, a 1-propylbutyl group, a sec-amyl group, an isoamyl group, a tert-amyl group, a neopentyl group, a 3-pentyl group, or a 1-butylpentyl group may be mentioned.

In addition, as the alkenyl group, for example, a vinyl group, an allyl group, or an isopropenyl group may be mentioned. As the alkynyl group, for example, an ethynyl group or a prop-2-yn-1-yl group may be mentioned. As the aryl group, for example, a phenyl group, a naphthyl group, an anthracenyl group, or a phenanthrenyl group may be mentioned. As the cycloalkyl group, for example, a cyclopropyl group, a cyclopentyl group, a cyclohexyl group, or a cycloheptyl group may be mentioned.

Any of the hydrocarbon groups may have a substituent. As the substituent, for example, an amino group, a halogen atom, a nitro group, a cyano group, an alkoxy group, an alkyl group, an alkenyl group, an alkynyl group, a cycloalkyl group, or an aryl group may be mentioned. In addition, as the halogen atom, for example, a fluorine atom, a chlorine atom, a bromine atom, or an iodine atom may be mentioned. As the alkoxy group, for example, a methoxy group or an ethoxy group may be mentioned.

As an alkyl-substituted aryl group, for example, a tolyl group may be mentioned. As an aryl-substituted alkenyl group, for example, a 3-phenyl-2-propenyl group may be mentioned.

As a carboxylic acid ester which can be used for the method for producing a carboxylic acid and an alcohol of the present invention, for example, there may be mentioned methyl laurate, ethyl laurate, isopropyl laurate, methyl 2-propylvalerate, ethylene glycol dilaurate, glycerol trioleate, 1-dodecyl acetate, 1-dodecyl propionate, 5-nonyl acetate, cinnamyl acetate, 1-(6-tert-butylphenylsilyloxy)dodecyl acetate, or 1-[6-(p-methoxybenzyl)oxy]dodecyl acetate.

In the method for producing a carboxylic acid and an alcohol of the present invention, the carboxylic acid ester may be an optically active carboxylic acid ester. According to the present invention, although the carboxylic acid ester is an optically active carboxylic acid ester, racemization can be prevented, and a carboxylic acid and/or an alcohol each having an optical activity can be obtained. Heretofore, in hydrolysis of an optically active carboxylic acid ester, since racemization occurs in association therewith, it has been difficult to produce an optically active carboxylic acid and/or an optically active alcohol in one step. That is, by the use of a protective group, a multi-step process has been inevitably performed. Hence, the present invention is significantly useful to produce a carboxylic acid and/or an alcohol each having an optical activity. An optically active carboxylic acid and an optically active alcohol are useful compounds functioning as intermediates of medicines and the like. As the optically active carboxylic acid ester, for example, the following esters may be mentioned by way of example, but the optically active ester is not limited thereto.

[Chem. 4]

In particular, the optically active carboxylic acid is preferably an α-amino acid ester. Since an optically active carboxylic acid obtained by hydrolysis of an α-amino acid ester is particularly liable to be racemized, in the past, the production has been carried out through multi-step reactions using a protective group. However, since the racemization can be prevented by the present invention, the protective group is not necessary, and hence the number of steps can be reduced. Since the optically active carboxylic acid obtained by hydrolysis of an α-amino acid ester is particularly useful as a medicine intermediate, in particular, the present invention can be preferably applied to medicine applications. As the α-amino acid ester, for example, although the following esters may be mentioned by way of example, the α-amino acid ester is not limited thereto.

[Chem. 5]

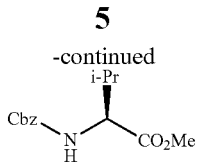

In particular, in the present invention, one of a carboxylic acid and an alcohol to be obtained is preferably water-soluble. When one of a carboxylic acid and an alcohol to be obtained is water-soluble, a hydrolysis reaction progresses with a high yield.

As the water-soluble carboxylic acid, for example, acetic acid, propionic acid, butyric acid, lactic acid, oxalic acid, citric acid, and tartaric acid may be mentioned; however, the water-soluble carboxylic acid is not limited thereto. Among those mentioned above, since an alcohol can be obtained with a high yield, acetic acid and propionic acid are particularly preferable.

In addition, as the water-soluble alcohol, for example, methanol, ethanol, 1-propanol, 2-propanaol, 1-butanol, 2-butanol, ethylene glycol, and glycerol may be mentioned; however, the water-soluble alcohol is not limited thereto. Among those mentioned above, methanol, ethanol, ethylene glycol, and glycerol, each of which has excellent water solubility, are preferable since a carboxylic acid can be obtained with a high yield.

Furthermore, the production method of the present invention may also be applied to a carboxylic acid ester which is unstable to a base. Hence, by hydrolysis of a carboxylic acid ester which has been difficult to be hydrolyzed in the past, a carboxylic acid and/or an alcohol can be obtained. As the carboxylic acid ester which is unstable to a base, for example, N-Fmoc-L-phenylalanine methyl ester may be mentioned; however, the unstable carboxylic acid ester is not limited thereto.

Next, an ammonium pyrosulfate catalyst used in the production method of the present invention is represented by the following general formula (1).

[Chem. 6]

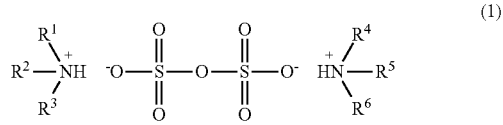

(1)

(In the formula, $R^1$ and $R^4$ each independently represent an aryl group, $R^2$, $R^3$, $R^5$, and $R^6$ independently represent an aryl group, an alkyl group, an alkenyl group, an alkynyl group, a cycloalkyl group, or a hydrogen atom.)

In addition, in the general formula (1), the positional relationship among $R^1$, $R^2$, and $R^3$ and the positional relationship between $R^4$, $R^5$, and $R^6$ are not particularly limited. In the above general formula (1), among the three substituents bonded to one N, at least one thereof represents an aryl group.

As the aryl group, for example, a phenyl group, a naphthyl group, an anthracenyl group, or a phenanthrenyl group may be mentioned. In particular, since having a high activity, a phenyl group is preferable. Those groups mentioned above each may have a substituent. Since the ammonium pyrosulfate catalyst forms a supramolecular structure in which an ammonium cationic portion functioning as a catalytic active portion and an ammonium pyrosulfate anion are covered with bulky and hydrophobic aryl groups using a plurality of hydrogen bonds, it is conceived that the ammonium pyrosulfate catalyst is stable even in the presence of a large amount of water and exhibits a high catalytic activity.

The aryl group preferably has at at least one ortho-position thereof, a branched alkyl group, a branched alkyl group having a substituent, a cycloalkyl group, a cycloalkyl group having a substituent, an aryl group, or an aryl group having a substituent. In this case, as the aryl group functioning as a substituent, for example, a phenyl group, a naphthyl group, an anthracenyl group, or a phenanthrenyl group may be mentioned. As the branched alkyl group, for example, an isopropyl group, an isobutyl group, a sec-butyl group, a tert-butyl group, 2-methyl-1-butyl group, a sec-amyl group, an isoamyl group, a tert-amyl group, a neopentyl group, or 3-pentyl group may be mentioned. As the cycloalkyl group, for example, a cyclopropyl group, a cyclopentyl group, a cyclohexyl group, or a cycloheptyl group may be mentioned. In addition, when the branched alkyl group has a substituent, as the substituent, for example, a halogen atom, a nitro group, a cyano group, an alkoxy group, a cycloalkyl group, or an aryl group may be mentioned. In addition, as the halogen atom, for example, a fluorine atom, a chlorine atom, a bromine atom, or an iodine atom may be mentioned. When the cycloalkyl group has a substituent, as the substituent, for example, a halogen atom, a nitro group, a cyano group, an alkoxy group, an alkyl group, a cycloalkyl group, or an aryl group may be mentioned. When the aryl group has a substituent, as the substituent, for example, a halogen atom, a nitro group, a cyano group, an alkoxy group, an alkyl group, a cycloalkyl group, or an aryl group may be mentioned. In addition, the aryl group may further have a substituent at the para-position. As the substituent at the para-position, for example, a branched alkyl group, a branched alkyl group having a substituent, a cycloalkyl group, a cycloalkyl group having a substituent, an aryl group, an aryl group having a substituent, or a halogen atom may be mentioned. As the halogen atom, for example, a fluorine atom, a chlorine atom, a bromine atom, or an iodine atom may be mentioned. Among those mentioned above, the branched alkyl group and the halogen atom are preferable. Among the branched alkyl groups, an isopropyl group is preferable, and among the halogen atoms, an iodine atom is preferable.

In addition, for example, since 2-(1,1'-binaphthyl) group may be regarded as a naphthyl group having a naphthyl group at an ortho-position, the above binaphthyl group may be regarded as one example of a naphthyl group having a substituent at an ortho-position. In this case, in consideration of a good hydrolysis yield of an ester compound, as the ammonium pyrosulfate, the aryl group is preferably a phenyl group having at the two ortho-positions, two substituents each selected from the group consisting of a branched alkyl group, an aryl group, and an aryl group having a substituent. In particular, a phenyl group having two substituents each selected from the group consisting of an isopropyl group and a phenyl group is preferable. In addition, the aryl group may have a halogen atom or a branched alkyl group at the para-position besides the substituents provided at the two ortho-positions. As the substituent at the para-position, in particular, an iodine atom or a phenyl group having an isopropyl group is preferable.

In addition, in the above general formula (1), the alkyl group is not particularly limited, and a linear or a branched alkyl group may be used. As the linear alkyl group, for example, a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, or an icosyl group may be mentioned.

As the branched alkyl group, for example, an isopropyl group, an isobutyl group, a sec-butyl group, a tert-butyl group, a 2-methyl-1-butyl group, a 1-propylbutyl group, a sec-amyl group, an isoamyl group, a tert-amyl group, a neopentyl group, a 3-pentyl group may be mentioned.

In addition, as the alkenyl group, for example, a vinyl group, an allyl group, or an isopropenyl group may be mentioned. As the alkynyl group, for example, an ethynyl group or a prop-2-yn-1-yl group may be mentioned. As the cycloalkyl group, for example, a cyclopropyl group, a cyclopentyl group, a cyclohexyl group, or a cycloheptyl group may be mentioned.

The alkyl group, the alkenyl group, the alkynyl group, and the cycloalkyl group each may have a substituent. As the substituent, for example, an amino group, a halogen atom, a nitro group, a cyano group, an alkoxy group, an alkyl group, a cycloalkyl group, or an aryl group may be mentioned. As the halogen atom, for example, a fluorine atom, a chlorine atom, a bromine atom, or an iodine atom may be mentioned.

In particular, the ammonium pyrosulfate catalyst is preferably an ammonium pyrosulfate catalyst represented by the following general formula (2)

[Chem. 7]

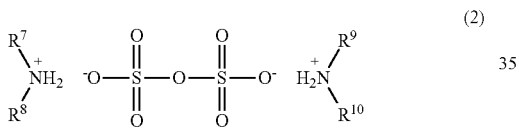

(2)

(in the formula, $R^7$, $R^8$, $R^9$, and $R^{10}$ each independently represent an aryl group). That is, in the above general formula (1), among the three substituents bonded to one N, two substituents each preferably represent an aryl group, and the other substituent preferably represents a hydrogen atom (in the above general formula (1), $R^1$ and $R^4$ each independently represent an aryl group, at least one of $R^2$ and $R^3$ and at least one of $R^5$ and $R^6$ each independently represent an aryl group, and the other one of $R^2$ and $R^3$ and the other one of $R^5$ and $R^6$ each represent a hydrogen atom). In this case, particularly preferable $R^7$, $R^8$, $R^9$, and $R^{10}$ are independently similar to the aryl groups described above as the preferable example. Since the ammonium pyrosulfate catalyst as described above forms a supramolecular structure in which an ammonium cationic portion functioning as a catalytic active portion and an ammonium pyrosulfate anion are covered in good balance with bulky and hydrophobic aryl groups, it is conceived that the ammonium pyrosulfate catalyst is significantly stable even in the presence of a large amount of water and exhibits a high catalytic activity.

Examples of the structural formula of the ammonium pyrosulfate as described above are shown below.

[Chem. 8]

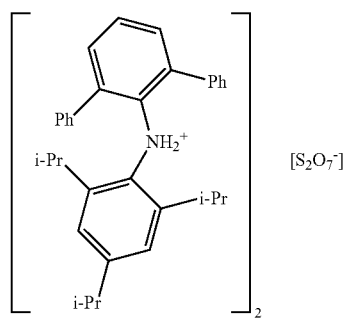

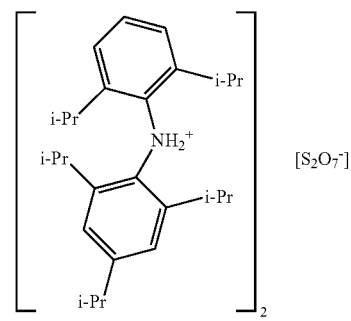

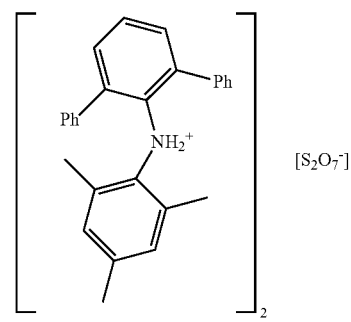

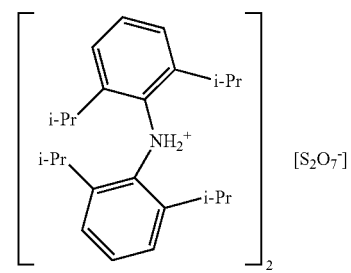

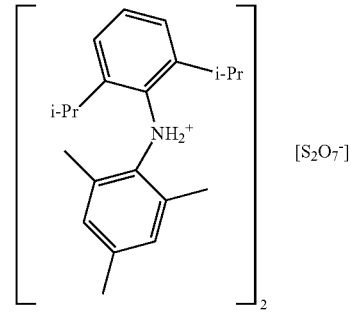

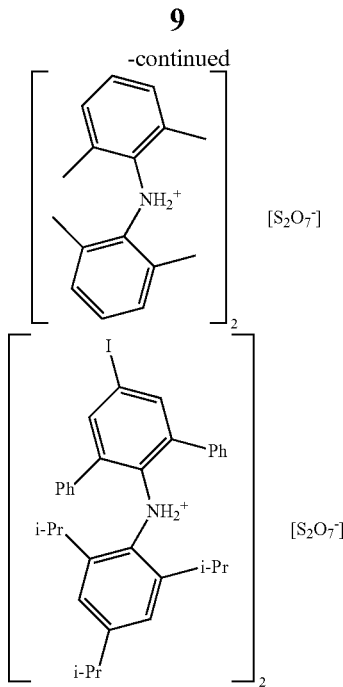

In the method for producing a carboxylic acid and an alcohol of the present invention, although the reaction temperature may be appropriately set in consideration of the reaction rate, the ratio of a by-product, and the like, for example, the reaction temperature may be set in a range of 20° C. to 100° C. and preferably in a range of 60° C. to 80° C. In addition, when a reaction substrate and a reaction product are compounds which are liable to be decomposed by heat, in order to prevent the decomposition thereof, the reaction temperature may be set in a range of 20° C. to 60° C. and preferably in a range of 30° C. to 50° C.

In the method for producing a carboxylic acid and an alcohol of the present invention, although the reaction time may be appropriately set in consideration of the reaction substrate, the reaction temperature, and the like, for example, the reaction time is generally several minutes to several tens of hours. A preferable reaction time is 10 to 60 hours and particularly 20 to 50 hours. In addition, although a hydrolysis reaction of a carboxylic acid ester may be performed until the carboxylic acid ester is totally consumed, when the reaction rate remarkably decreases as the reaction proceeds, even if the carboxylic acid ester is not totally consumed, in some cases, the reaction may be preferably stopped so as to recover a carboxylic acid and/or an alcohol.

In addition, although the amount of the catalyst is not particularly limited, with respect to the carboxylic acid ester, the amount of the catalyst is 0.5 to 15 mol %, preferably 1 to 10 mol %, and particularly 3 to 8 mol %. When the amount is smaller than the range described above, the activity is inferior, and on the other hand, even when the amount is larger than this range, since the reactivity is not improved, it is not economical.

Furthermore, although the amount of water used as a solvent is not particularly limited, with respect to 1 mmol of the carboxylic acid ester, the amount of water can be set in a range of 0.1 to 10 mL, preferably in a range of 1 to 5 mL, and particularly in a range of 2 to 4 mL. When the amount is smaller than the range described above, the activity is inferior, and on the other hand, even when the amount is larger than this range, the reactivity is not improved.

In the method for producing a carboxylic acid and an alcohol of the present invention, in order to isolate targeted carboxylic acid and alcohol, an isolation method which has been commonly known may be used. For example, by decantation performed after neutralization of the catalyst, isolation can be easily performed. The obtained carboxylic acid and/or alcohol can be refined by a column chromatography, if needed.

According to the production method of the present invention, since water is only used as a reaction solvent, and an organic solvent is not required, besides reduction in cost, no environmental issues exist, and no waste liquid treatment is required. In addition, in the production process, the safety can be significantly secured. In addition, according to the production method of the present invention, since production can be performed under an acidic condition unlike the case in which a base is used, by use of catalyst quantity, the production can be performed with a high yield, and hence the production efficiency is improved.

Next, the catalyst to produce a carboxylic acid and an alcohol of the present invention has the structure similar to that of the ammonium pyrosulfate described in the above method for producing a carboxylic acid and an alcohol. The ammonium pyrosulfate has a high activity for a hydrolysis reaction of a carboxylic acid ester in an aqueous solvent without using a base. Hence, this ammonium pyrosulfate can be preferably used for production of a carboxylic acid and an alcohol. A particularly preferable catalyst is similar to the ammonium pyrosulfate which is preferably used in the above production method. That is, $R^{11}$, $R^{12}$, $R^{13}$, $R^{14}$, $R^{50}$, and $R^{16}$ in the above general formula (3) representing the ammonium pyrosulfate correspond to $R^1$, $R^2$, $R^3$, $R^4$, $R^5$, and $R^6$ of the above general formula (1), respectively.

The ammonium pyrosulfate functioning as a catalyst may be produced, for example, as described below. That is, in a first production method, an amine represented by the following general formula (4)

[Chem. 9]

(4)

(in the formula, $R^{17}$ represents an aryl group, and $R^{18}$ and $R^{19}$ each independently represent an aryl group, an alkyl group, an alkenyl group, an alkynyl group, a cycloalkyl group, or a hydrogen atom) and sulfuric acid are dissolved in an organic solvent and are then heated to 60° C. to 100° C.

Alternatively, in a second production method, an amine represented by the following general formula (4)

[Chem. 10]

(4)

(in the formula, $R^{17}$ represents an aryl group, and $R^{18}$ and $R^{19}$ each independently represent an aryl group, an alkyl group, an alkenyl group, an alkynyl group, a cycloalkyl group, or a hydrogen atom) and fuming sulfuric acid are brought into contact with each other.

The amines used in the method for producing an ammonium pyrosulfate each can be represented by the following general formula (4)

[Chem. 11]

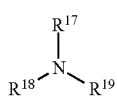
(4)

(in the formula, $R^{17}$ represents an aryl group, and $R^{18}$ and $R^{19}$ each independently represent an aryl group, an alkyl group, an alkenyl group, an alkynyl group, a cycloalkyl group, or a hydrogen atom).

A preferable aryl group is similar to the preferable aryl group of the ammonium pyrosulfate used in the above-described method for producing a carboxylic acid and an alcohol. In particular, an aryl group having at at least one ortho-position, a branched alkyl group, a branched alkyl group having a substituent, a cycloalkyl group, a cycloalkyl group having a substituent, an aryl group, or an aryl group having a substituent is preferable. In particular, the amine is preferably a secondary amine in which one of $R^{18}$ or $R^{19}$ represents an aryl group. As examples of the amine described above, the following secondary amines may be mentioned.

[Chem. 12]

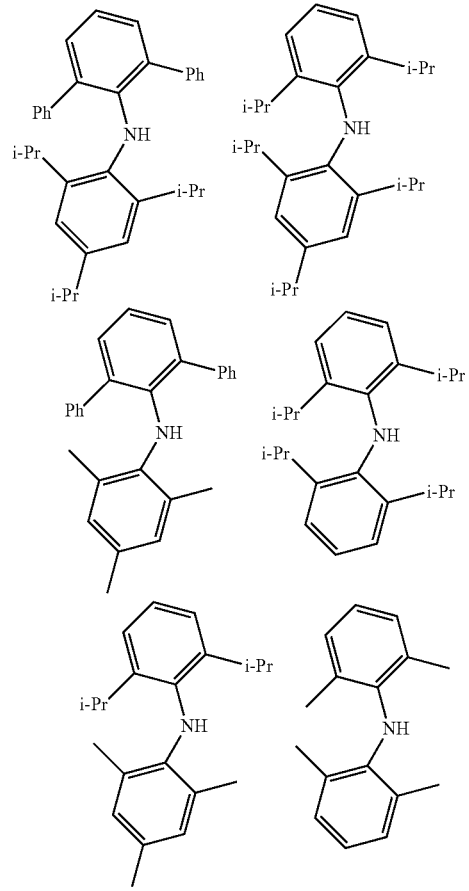

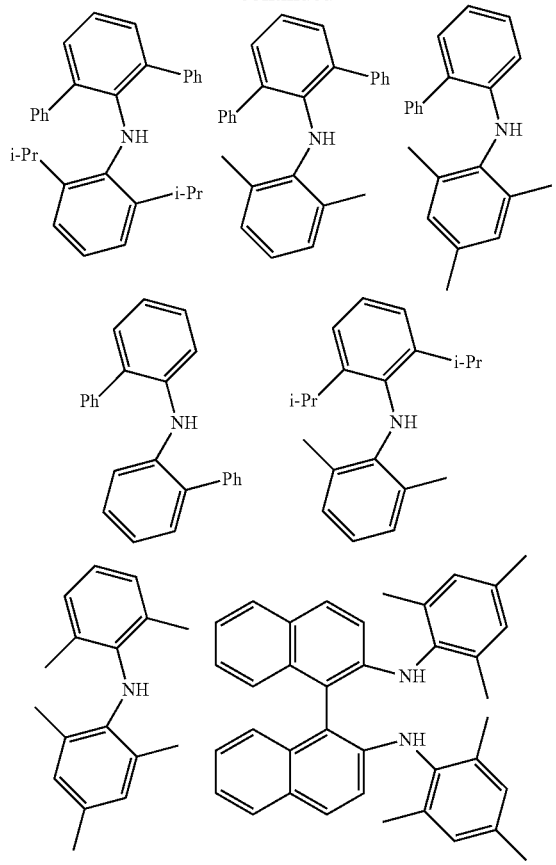

Furthermore, as a tertiary amine, the following tertiary amines may be mentioned by way of example. In the tertiary amine, when all substituents are each an aryl group or an aryl group having a substituent, aryl groups each having an alkyl group at the para-position are not preferable since the reactivity of the amine is inferior.

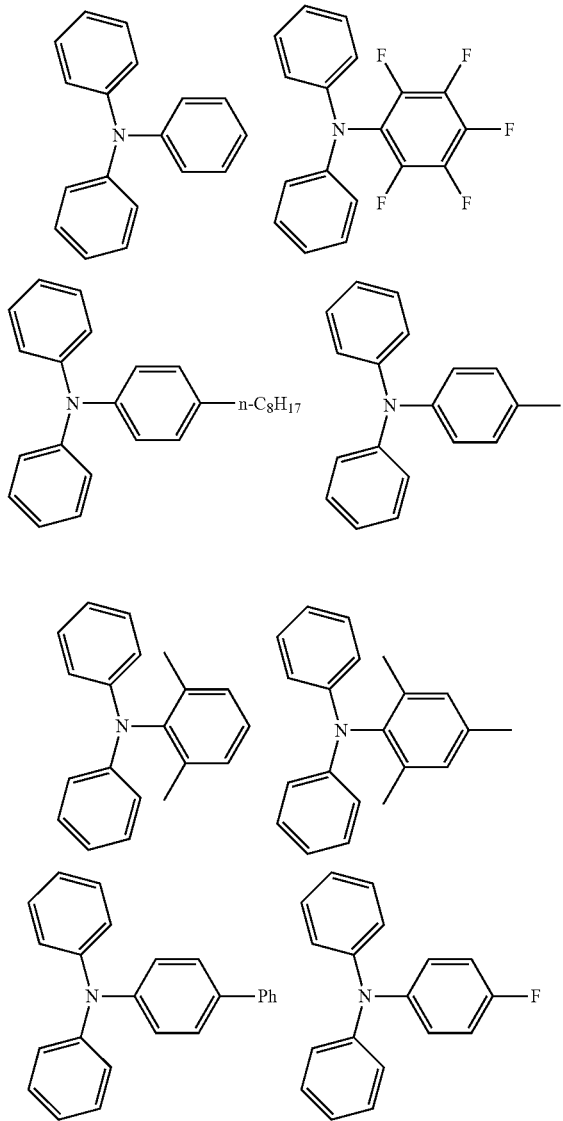

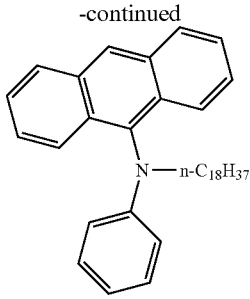

In addition, examples of a tertiary amine in which one of $R^{18}$ and $R^{19}$ represents an aryl group, and the other one represents an alkyl group are shown below. In this case, in consideration of commercial availability and good yield, the number of carbon atoms of the alkyl group is preferably 8 to 20.

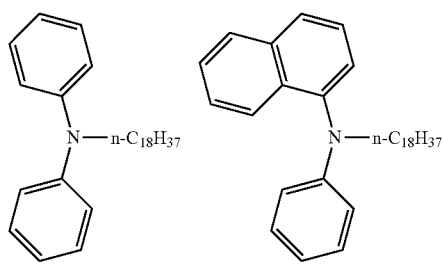

In the first method for producing an ammonium pyrosulfate, although not particularly limited, the amount of the amine and that of the sulfuric acid in a molar ratio is preferably 0.5:3 to 3:0.5, more preferably 1:2 to 2:1, and particularly preferably 1:1. Even when the amount of one of the above materials is larger than the range described above, it is not economical since a production rate is not improved. The sulfuric acid to be used is not particularly limited, and a commercially available or a synthesized product may be used.

In addition, the reaction temperature is required to be set in a range of 50° C. to 100° C. When the reaction temperature is lower than that described above, a catalyst having a high activity cannot be obtained. On the other hand, even when the reaction temperature is higher than that described above, it is not appropriate since the yield is not improved. The reaction temperature can be preferably set in a range of 60° C. to 80° C. According to the present invention, it was found that when heating is performed in a predetermined temperature range, an ammonium pyrosulfate having a high catalytic activity is produced, and an excellent activity is exhibited.

An organic solvent which can be used for the first method for producing an ammonium pyrosulfate is not particularly limited, and any commonly known organic solvents may be used. For example, there may be mentioned a hydrocarbon-based solvent, such as benzene, toluene, xylene, or chlorobenzene; a nitrile-based solvent, such as acetonitrile or propionitrile; a halogenated hydrocarbon-based solvent, such as dichloromethane, 1,2-dichloroethane, chloroform, carbon tetrachloride, chlorobenzene, or bromobenzene; and an ether-based solvent, such as tetrahydrofuran or 1,4-dioxane. Those mentioned above may be used alone, or at least two of them may be used by mixing. In particular, since having a good solubility to sulfuric acid, an amine, and an ammonium pyrosulfate, for example, 1,4-dioxane is preferable.

In addition, although the amount of the solvent is not particularly limited, with respect to 1 mole of the substrate (amine), the amount of the solvent can be preferably set in a range of 0.1 to 10 L and particularly in a range of 1 to 4 L.

Although the reaction time may be appropriately set in accordance with the reaction substrate, the reaction temperature, and the like, the reaction time is generally several minutes to several hours, preferably 10 to 60 minutes, and particularly 20 to 40 minutes.

In the first method for producing an ammonium pyrosulfate, the solvent can be removed from a targeted product. For example, the solvent is preferably distilled off under reduced pressure. According to the first production method, since the sulfuric acid used for the catalyst production is inexpensive, the manufacturing cost thereof can be reduced.

Furthermore, the fuming sulfuric acid used for the second method for producing an ammonium pyrosulfate of the present invention may be either a commercial available or a synthesized fuming sulfuric acid and is not particularly limited. Although the concentration of $SO_3$ contained in the fuming sulfuric acid is not particularly limited, for example, since being commercially available, a product having a concentration of 60% to 25% and particularly 30% is preferable.

In the second method for producing an ammonium pyrosulfate, although the amount of the amine and that of the fuming sulfuric acid is not particularly limited, the molar ratio therebetween is preferably 0.5:3 to 3:0.5, more preferably 1:2 to 2:1, and particularly preferably 1:1. Even if one of the above two is larger than the range described above, since the production rate is not improved, it is not economical.

Although a method for contacting the amine and the fuming sulfuric acid is not particularly limited, for example, when being dissolved in an organic solvent, the amine and the fuming sulfuric acid can be brought into contact with each other. Although the temperature is not particularly limited, from an economical point of view, and in consideration of prevention of $SO_3$ emission and the like, the contact is preferably performed at room temperature. According to the second method for producing an ammonium pyrosulfate of the present invention, since the production can be performed at room temperature, heating is not required, and hence the ammonium pyrosulfate can be easily produced.

The contact time is a time in which the catalyst can be produced and may be appropriately set in accordance with the reaction temperature, the reaction substrate, and the like; however, in general, the contact time is several minutes to several hours. The contact time is preferably 10 to 60 minutes and particularly 20 to 40 minutes. In the case in which the amine and the like are dissolved in a solvent, an organic solvent to be used, the amount thereof, and a method for removing a solvent are similar to those described in the above first method for producing an ammonium pyrosulfate.

EXAMPLES

Example 1

Preparation of Ammonium Pyrosulfate Catalyst (1) First Manufacturing Method

[Chem. 15]

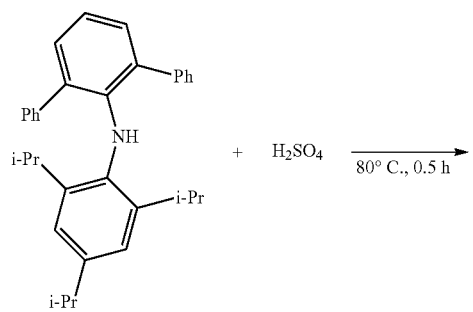

(6)

-continued

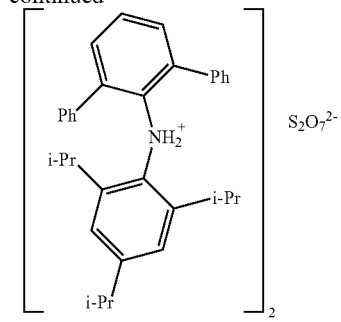

As shown in the above formula (6), after N,N-diarylamine (0.10 mmol, 5 mol %) and sulfuric acid (0.10 mmol, mol %) were weighed in a flask and were then dissolved in 1,4-dioxane (0.1 mL), stirring was performed at 80° C. for 30 minutes. After the mixture thus obtained was cooled to room temperature, 1,4-dioxane was distilled off under reduced pressure. The ammonium pyrosulfate thus obtained was analyzed by $^1$H NMR ($CD_3CN$). The chemical shifts (ppm) thereof are shown below.

δ 0.89 (d, J=6.9 Hz, 12H), 1.07 (d, J=6.9 Hz, 6H), 2.63 (septet, J=6.9 Hz, 1H), 2.86 (septet, J=6.9 Hz, 2H), 6.57 (s, 2H), 7.01 (t, J=7.3 Hz, 1H), 7.10 (d, J=7.3 Hz, 2H), 7.18-7.31 (m, 10H), 9.01 (s, 2H).

(2) Second Manufacturing Method

Except that 30% $SO_3$-containing fuming sulfuric acid was used instead of sulfuric acid, and the temperature was set to room temperature (20° C.), production was performed in a manner similar to that of the above first production method (1), and the analysis was then performed. The chemical shifts were approximately identical to those of the ammonium pyrosulfate obtained by the production method (1) of Example 1. The chemical shifts (ppm) are shown below. Hence, it is found that the structure is similar to that of the ammonium pyrosulfate obtained by the production method (1) of Example 1.

δ 0.95 (d, J=6.9 Hz, 12H), 1.05 (d, J=6.9 Hz, 6H), 2.61 (septet, J=6.9 Hz, 1H), 2.90 (septet, J=6.9 Hz, 2H), 6.54 (s, 2H), 7.04-7.31 (m, 9H), 7.37 (d, J=6.8 Hz, 4H), 9.23 (s, 2H).

Comparative Example 1

Preparation of Ammonium Salt Catalyst Performed at Room Temperature

In a manner similar to that of the above Example 1, after N,N-diarylamine (0.10 mmol, 5 mol %) and sulfuric acid (0.10 mmol, 5 mol %) were weighed in a flask and were then dissolved in 1,4-dioxane (0.1 mL), stirring was performed at room temperature (approximately 20° C.) for 30 minutes. Subsequently, 1,4-dioxane was distilled off under reduced pressure. The ammonium salt thus obtained was analyzed by $^1$H NMR ($CD_3CN$). The chemical shifts (ppm) thereof are shown below. Since the chemical shift (7.59 ppm) of an ammonium proton is remarkably different from those (9.01, 9.23 ppm) of the ammonium pyrosulfates obtained by the manufacturing methods (1) and (2) of Example 1, it is found that the structure is different therefrom.

δ 0.84 (d, J=6.8 Hz, 12H), 1.11 (d, J=6.9 Hz, 6H), 2.71 (septet, J=6.9 Hz, 2H), 2.75 (septet, J=6.9 Hz, 1H), 6.67 (s, 2H), 7.18-7.35 (m, 5H), 7.26-7.58 (m, 8H), 7.59 (s, 2H).

Example 2

Production of Lauric Acid (and Methanol) by Hydrolysis of Methyl Laurate

After methyl laurate (2 mmol) and water (1 to 8 mL) were added to the ammonium pyrosulfate catalyst (5 mol %) obtained in Example 1(1), heating was performed at 60° C. for 24 hours while stirring was performed, so that a hydrolysis reaction of methyl laurate was performed. The reaction mixture thus obtained was partly sampled and was analyzed by $^1$H NMR (CDCl$_3$), so that the yield of lauric acid was calculated. The chemical shifts (ppm) are shown below. In addition, the results are shown in Table 1.

Methyl laurate: δ 0.88 (t, J=6.6 Hz, 3H), 1.29 (m, 16H), 1.62-1.65 (m, 2H), 2.30 (t, J=7.5 Hz, 2H), 3.66 (s, 3H)

Lauric acid: δ 0.89 (t, 3H), 1.16-1.37 (m, 16H), 1.64 (q, J=7.3, 2H), 2.35 (t, J=7.3 Hz, 2H)

TABLE 1

| Amount of water (mL) | 1 | 2 | 4 | 8 |
|---|---|---|---|---|
| Yield (%) | 55 | 66 | 73 | 86 |

As apparent from Table 1, it is found that when the amount of water to be used with respect to 2 mmol of methyl laurate is increased, the yield is increased, and in the water volume between 1 to 8 mL, a highest yield of 86% is obtained at a water volume of 8 mL.

Comparative Example 2

Production of Lauric Acid (and Methanol) by Hydrolysis of Methyl Laurate by Another Catalyst Under reaction conditions similar to those of the above Example 2, instead of using the ammonium pyrosulfate catalyst, sulfuric acid (H$_2$SO$_4$, 5 mol %), dodecylbenzene sulfuric acid (DBSA, 5 mol %), lithium hydroxide (LiOH, 100 mol %), and a mixture (LiOH (100 mol %)+Bu$_4$NBr (5 mol %)) of lithium hydroxide (LiOH) and tetrabutylammonium bromide were used, and a reaction was performed for 20 to 26 hours. The results are shown in Table 2.

TABLE 2

| Catalyst | Time (h) | Yield (%) |
|---|---|---|
| Ammonium pyrosulfate (5 mol %) | 20 | 86 |
| Sulfuric acid (5 mol %) | 20 | 4 |
| Dodecylbenzene sulfuric acid (5 mol %) | 26 | 76 |
| Lithium hydroxide (100 mol %) | 20 | 6 |
| Lithium hydroxide (100 mol %) + Tetrabutylammonium bromide (5 mol %) | 20 | 3 |

As apparent from Table 2, sulfuric acid (5 mol %) and lithium hydroxide (100 mol %) each showed a remarkably low activity. Even when tetrabutylammonium bromide (5 mol %) was added as a phase transfer catalyst to lithium hydroxide, the reactivity was not improved. Although hydrolysis progressed when dodecylbenzene sulfuric acid (DBSA) functioning to promote ester dehydration condensation in water was added, the yield was low as compared to that of the case in which the N,N-diarylammonium salt catalyst of the Example 1 was used. In addition, since separation of DBSA is not easily performed after the reaction, and a post treatment thereof is also complicated, the handling property of DBSA is inferior to that of the catalyst of this example. Incidentally, an ester dehydrative condensation method in water using DBSA as a catalyst has been disclosed in literatures (J. Am. Chem. Soc. 2001, 123, 10101 to 10102 and J. Am. Chem. Soc. 2002, 124, 11971 to 11978). On the other hand, when hydrolysis of methyl laurate was performed in a manner similar to that described above by using the ammonium salt produced in Comparative Example 1, the yield was 3%, and hence it is found that the activity is low.

Example 3

Production of Carboxylic Acid and Water-Soluble Alcohol by Hydrolysis of Carboxylic Acid Ester As shown in the following Table 3, by using carboxylic acid esters, each of which produced a water-soluble alcohol, a hydrolysis reaction of a carboxylic acid ester was performed. That is, 1 mmol of the carboxylic acid ester and 4 mL of water were added to the ammonium pyrosulfate catalyst (5 mol %) obtained in Example 1(1), and the mixture was heated at 60° C. to 80° C. for 24 to 48 hours while stirring was performed. The reaction mixture thus obtained was partly sampled and was analyzed by $^1$H NMR (CDCl$_3$), and by comparison between the following signals, the yield of a carboxylic acid was calculated. The chemical shifts (ppm) are shown below. In addition, the results are shown in Table 3.

1. Ethyl laurate: δ 2.29 (t, J=7.7 Hz, 2H)

Lauric acid: δ 2.35 (t, J=7.3 Hz, 2H)

2. Isopropyl laurate: δ 2.25 (t, J=7.5 Hz, 3H)

Lauric acid: δ 2.35 (t, J=7.3 Hz, 2H)

3. Ethylene glycol dilaurate: δ 2.31 (t, J=7.8 Hz, 4H)

Lauric acid: δ 2.35 (t, J=7.3 Hz, 2H)

4. Glycerol trioleate: δ 2.31 (t, J=6.9 Hz, 4H), 2.32 (t, J=7.5 Hz, 2H)
  Oleic acid: δ 2.35 (t, J=7.3 Hz, 2H)
5. Glycerol tripalmitate: δ 2.31 (t, J=7.3 Hz, 6H)
  Palmitic acid: δ 2.34 (t, J=7.3 Hz, 2H)
6. Glycerol trilinoleate: δ 2.31 (t, J=7.3 Hz, 6H)
  Linoleic acid: δ 2.34 (t, J=7.6 Hz, 2H)
7. Methyl 2-propylvalerate: δ 2.21 (m, 1H), 3.67 (s, 3H)
  2-Propylvaleric acid: δ 2.37 (m, 1H)

TABLE 3

$$R'\text{-CO-OR''} \xrightarrow[\text{H}_2\text{O (4 mL)}]{\text{Ammonium pyrosulfate catalyst (5 mol \%)}} R'\text{-CO-OH}$$

1 mmol

| | Ester (R'CO₂R'') | | Temperature (°C.) | Time (h) | Yield (%) |
|---|---|---|---|---|---|
| 1 | CH₃(CH₂)₁₀C(O)OEt | | 60 | 20 | 83 |
| 2* | CH₃(CH₂)₁₀C(O)Oi—Pr | | 80 | 30 | 85 |
| 3 | CH₃(CH₂)₁₀C(O)OCH₂CH₂OC(O)(CH₂)₁₀CH₃ | | 60 | 24 | 92 |
| 4 | Glycerol triester | [R = (CH₂)₇CH=CH(CH₂)₇CH₃] | 80 | 24 | 86 |
| 4a** | Glycerol triester | [R = (CH₂)₇CH=CH(CH₂)₇CH₃] | 80 | 56 | 82 |
| 5 | Glycerol triester | [R = (CH₂)₁₄CH₃] | 80 | 24 | 95 |
| 6 | Glycerol triester | [R = (CH₂)₇CH=CHCH₂CH=CH(CH₂)₄CH₃] | 80 | 24 | 90 |

TABLE 3-continued

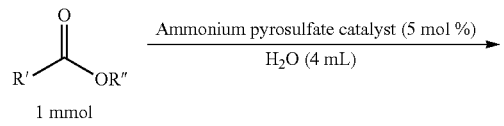

| | Ester (R'CO₂R") | Temperature (° C.) | Time (h) | Yield (%) |
|---|---|---|---|---|
| 7 | 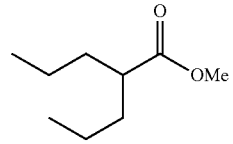 | 80 | 48 | 92 |

*8 mL of water was used as a catalyst
**100 mmol of the ester was used by scale-up, 3 mol % of the catalyst and 400 mL of water as a solvent.

As apparent from Table 3, it is found that carboxylic acid esters, each of which produces a water-soluble alcohol by hydrolysis, are each hydrolyzed with a high efficiency, and a carboxylic acid can be obtained with a high yield. In addition, when 100 mmol of the carboxylic acid ester (glycerol trioleate) was used by scale-up, the reaction preferably progressed even by 3 mol % of the catalyst.

Example 4

Production of Alcohol and Water-Soluble Carboxylic Acid by Hydrolysis of Carboxylic Acid Ester As shown in the following Table 4, a hydrolysis reaction was performed using carboxylic acid esters, each of which produced a water-soluble carboxylic acid. That is, 1 mmol of the carboxylic acid ester and 4 mL of water were added to the ammonium pyrosulfate catalyst (5 mol %) obtained in Example 1(1), and heating was performed at 40° C. to 80° C. for 24 hours while stirring was performed. The reaction mixture thus obtained was partly sampled and was analyzed by ¹H NMR (CDCl₃), and by comparison between the following signals, the yield of an alcohol was calculated. The chemical shifts (ppm) are shown below. In addition, the results are shown in Table 4.

1. 1-Dodecyl acetate: δ 4.05 (t, J=6.6 Hz, 2H)
   1-Dodecanol: δ 3.64 (t, J=6.4 Hz, 2H)
2. 1-Dodecyl propionate: δ 4.18 (t, J=6.1 Hz, 2H)
   1-Dodecanol: δ 3.64 (t, J=6.4 Hz, 2H)
3. 5-Nonyl acetate: δ 4.89 (m, 1H)
   5-Nonanol: δ 3.56-3.59 (m, 1H)
4. 6-TBDPO-1-hexyl acetate: δ 4.03 (t, J=6.4 Hz, 2H)
   6-TBDPO-1-hexanol: δ 3.61 (t, J=6.6 Hz, 2H)
5. 6-PMBO-1-hexyl acetate: δ 4.02 (t, J=6.9 Hz, 2H)
   6-PMBO-1-hexanol: δ 3.63 (t, J=6.5 Hz, 2H)
6. Cinnamyl acetate: δ 4.73 (dd, J=1.1, 6.5 Hz, 2H)
   Cinnamyl alcohol: δ 4.32 (dd, J=1.5, 5.7 Hz, 2H)

TABLE 4

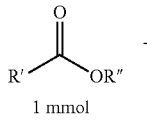

| | Ester (R'CO₂R") | Temperature (° C.) | Time (h) | Yield (%) |
|---|---|---|---|---|
| 1 | 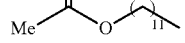 | 60 | 6 | 85 |
| 2* |  | 60 | 30 | 74 |
| 3 | 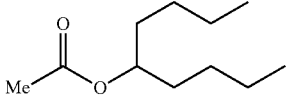 | 80 | 24 | 89 |
| 4* | 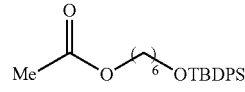 | 40 | 30 | 88 |
| 5 | 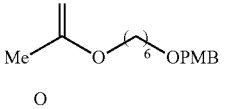 | 40 | 30 | 86 |
| 6 | 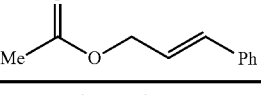 | 40 | 24 | 93 [2] |

*8 mL of water was used as a catalyst.

As apparent from Table 4, it is found that the carboxylic acid esters, each of which produces a water-soluble carboxylic acid by hydrolysis, are hydrolyzed with a high efficiency, and alcohols can be obtained with a high yield. In addition, in a hydrolysis reaction shown in the bottom portion of Table 4 in which cinnamyl acetate is used as the carboxylic acid ester, since cinnamyl alcohol, which is a reaction product, may be dimerized to form dicinnamyl ether as a by-product in some cases, a reaction was taken place at a low temperature of 40° C.; however, an alcohol could be obtained with a high yield of 93%. In the above table, the yield shown in the parentheses indicates the yield of dicinnamyl ether.

Example 5

Production of Optically Active Carboxylic Acid by Hydrolysis of Optically Active Carboxylic Acid Ester As shown in the following Table 5, by using 1 mmol of optically active carboxylic acid esters, each of which produced an optically active carboxylic acid, a hydrolysis reaction of a carboxylic acid ester was performed. That is, 1 mmol of the carboxylic acid ester and 4 mL of water were added to the ammonium pyrosulfate catalyst (5 mol %) obtained in Example 1(1), and the mixture was heated at 80° C. for 9 to 20 hours while stirring was performed. The reaction mixture thus obtained was diluted with water and was then extracted with ethyl acetate. After organic layers were collected and dried with sodium sulfate, a crude product obtained by condensation under reduced pressure was purified by a column chromatography, so that an optically active carboxylic acid was obtained. In addition, the optical purity of the reaction product was measured by a chiral HPLC. Characteristic chemical shifts (ppm) by $^1$H NMR (CDCl$_3$) and the analytical conditions of the chiral HPLC are shown below. In addition, the results are shown in Table 5.

1, 2. (S)-2-Methoxy-2-phenylacetatic acid methyl ester: δ 3.41 (s, 3H)

(S)-2-Methoxy-2-phenylacetatic acid: δ 3.33 (s, 3H); HPLC (Daicel Chiralcel OJ-H, hexane.i-PrOH 200: 1, 1 mL/min) t=33.1 [S-enantiomer], 37.5 [R-enantiomer] min 3, 4.N-Cbz-L-phenylglycine methyl ester: δ 3.73 (s, 3H), 5.38 (d, J=7.3 Hz, 1H)

N-Cbz-L-phenylglycine: δ 5.40 (d, J=6.9 Hz, 1H); HPLC (Daicel Chiralcel OJ-H, hexane.i-PrOH.TFA 75: 25: 0.1, 1.0 mL/min) t=16.6 [L-enantiomer], 12.5 [D-enantiomer] min 5, 6.N-Cbz-O-benzyl-L-serine methyl ester: δ 5.12 (s, 2H), 3.75 (s, 3H)

N-Cbz-O-benzyl-L-serine: δ 5.13 (s, 2H); HPLC (Daicel Chiralcel OD-H, hexane.i-PrOH.TFA 90: 10: 0.1, 1 mL/min) t=18.7 [S-enantiomer], 24.6 [R-enantiomer] min 7, 8.N-Fmoc-L-phenylalanine methyl ester: δ 3.10 (m, 1H), 3.15 (m, 1H), 3.74 (s, 3H)

N-Fmoc-L-phenylalanine: δ 3.13 (m, 1H), 3.22 (m, 1H); HPLC (Daicel Chiralcel OD-H, hexane.i-PrOH.TFA 90: 10: 0.1, 1.0 mL/min) t=16.5 [L-enantiomer], 12.9 [D-enantiomer] min 9. N-Cbz-L-phenylalanine methyl ester: δ 3.10 (m, 2H), 3.71 (s, 3H)

N-Cbz-L-phenylalanine: δ 3.12 (m, 1H), 3.21 (m, 1H); HPLC (Daicel Chiralcel OD-H, hexane.i-PrOH.TFA 90: 10: 0.1, 0.8 mL/min) t=26.3 [L-enantiomer], 22.9 [D-enantiomer] min 10. N-Cbz-L-valine methyl ester: δ 2.11 (m, 1H), 3.68 (s, 3H)

N-Cbz-L-valine: δ 2.23 (m, 1H); HPLC (Daicel Chiralpak OD-H, hexane.i-PrOH.TFA 90: 10: 0.1, 1.0 mL/min) t=6.0 [L-enantiomer], 12.0 [D-enantiomer] min

TABLE 5

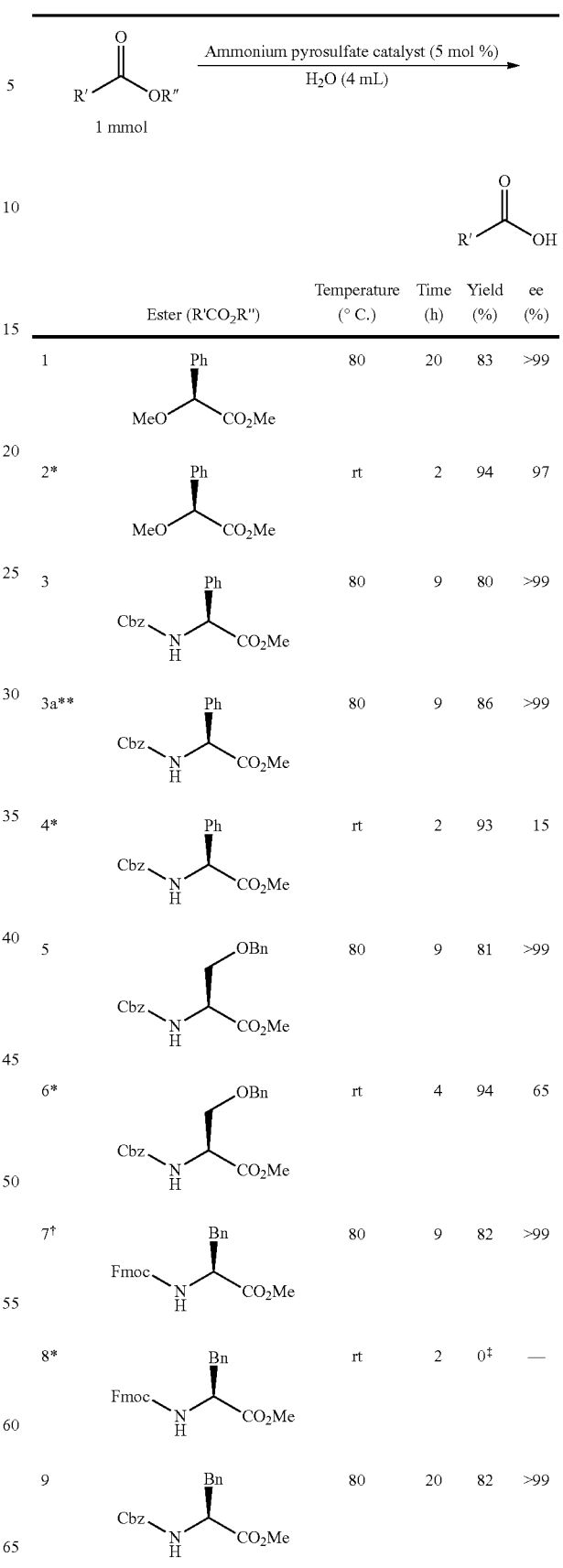

| | Ester (R'CO$_2$R") | Temperature (° C.) | Time (h) | Yield (%) | ee (%) |
|---|---|---|---|---|---|
| 1 | Ph, MeO, CO$_2$Me | 80 | 20 | 83 | >99 |
| 2* | Ph, MeO, CO$_2$Me | rt | 2 | 94 | 97 |
| 3 | Ph, Cbz-NH, CO$_2$Me | 80 | 9 | 80 | >99 |
| 3a** | Ph, Cbz-NH, CO$_2$Me | 80 | 9 | 86 | >99 |
| 4* | Ph, Cbz-NH, CO$_2$Me | rt | 2 | 93 | 15 |
| 5 | OBn, Cbz-NH, CO$_2$Me | 80 | 9 | 81 | >99 |
| 6* | OBn, Cbz-NH, CO$_2$Me | rt | 4 | 94 | 65 |
| 7† | Bn, Fmoc-NH, CO$_2$Me | 80 | 9 | 82 | >99 |
| 8* | Bn, Fmoc-NH, CO$_2$Me | rt | 2 | 0‡ | — |
| 9 | Bn, Cbz-NH, CO$_2$Me | 80 | 20 | 82 | >99 |

TABLE 5-continued $$R'\overset{O}{\underset{}{\text{C}}}OR'' \xrightarrow[H_2O\ (4\ mL)]{\text{Ammonium pyrosulfate catalyst (5 mol \%)}}$$
1 mmol $$R'\overset{O}{\underset{}{\text{C}}}OH$$

| Ester (R'CO₂R'') | Temperature (° C.) | Time (h) | Yield (%) | ee (%) |
|---|---|---|---|---|
| 10   Cbz-NH-CH(i-Pr)-CO₂Me | 80 | 9 | 86 | >99 |

*Instead of using the ammonium pyrosulfate catalyst, lithium hydroxide (100 mol %) was used, the reaction was taken place in a solvent containing H₂O—MeOH—THF (2:1:1).
**100 mmol of the ester was used by scale-up, 1 mol % of the catalyst and 400 mL of water were used as a solvent.
†Nitroethane(0.3 mL) was added for dissolve ester and the reaction was taken place.
‡Fmoc group was totally decomposed, phenylalanine was generated.

As apparent from Table 5, the optically active carboxylic acid esters, each of which produced an optically active carboxylic acid by hydrolysis, were each hydrolyzed with a high efficiency. In addition, it is found that although the carboxylic acid thus obtained is liable to be racemized under a basic condition, since the enantiomeric excess is significantly high, such as more than 99%, the racemization can be prevented. Furthermore, when 100 mmol of the carboxylic acid ester (N-Cbz-L-phenylglycine methyl ester) was used by scale-up, the reaction preferably progressed even by 1 mol % of the catalyst.

On the other hand, as comparative examples, the results of hydrolysis reactions in which the same carboxylic acid esters as those of 1, 3, 5, and 7 were hydrolyzed at room temperature for 2 to 4 hours in a solvent containing $H_2O$, NeOH, and THF (2:1:1) by the use of one equivalent of lithium hydroxide (LiOH) as a base are shown in 2*, 4*, 6*, and 8* of Table 5. As apparent from Table 5, although a high yield of 94% was obtained in 2*, since the enantiomeric excess was 97%, it is found that the racemization partly occurred. In addition, although high yields of 93% and 94% were obtained also in 4* and 6*, respectively, since the enantiomeric excess were 15% and 65%, respectively, it is found that the racemization occurred. In addition, since the Fmoc group functioning as a protective group for the amino group was totally decomposed in 8*, a targeted carboxylic acid could not be obtained at all. Hence, it is found that the production method of this embodiment is significantly useful to obtain an optically active carboxylic acid by preventing the racemization.

Example 6

Production and Reactivity of Catalyst Having Iodine Atom at Para-Position of Phenyl Group

[Chem. 16]

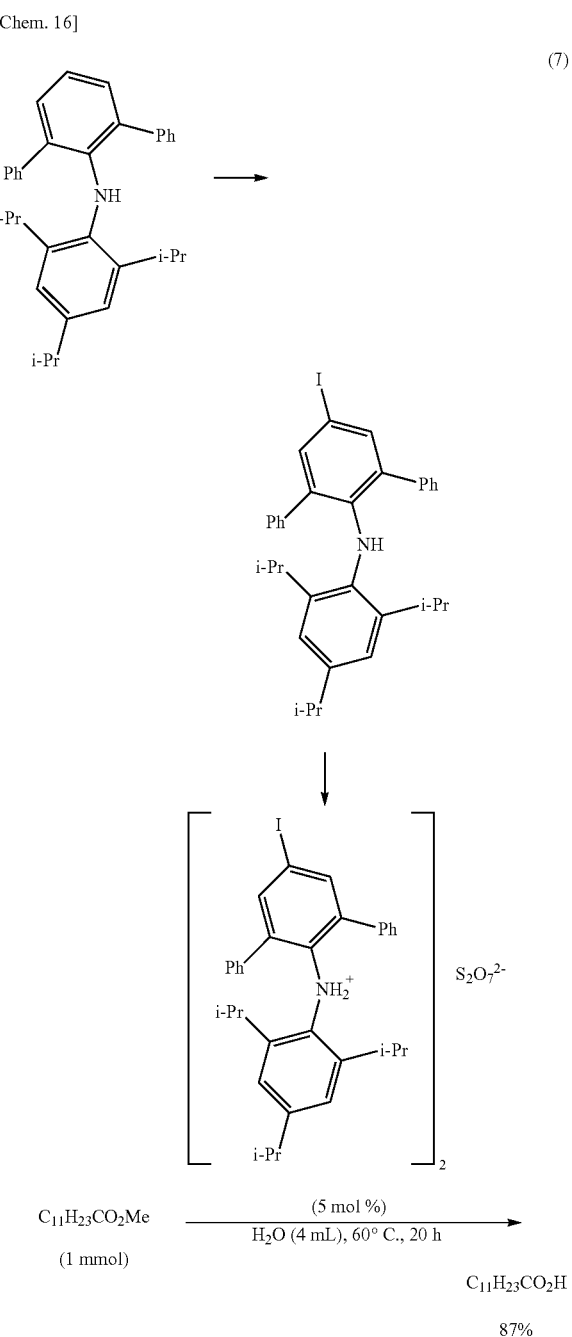

First, an N,N-diarylamine having an iodine atom at the para-position of a phenyl group was synthesized by the following procedure in accordance with an upper stage of the formula (7). The N,N-diarylamine (447 mg, 1.0 mmol) used in the formula (6) of Example 1 and calcium carbonate (150 mg, 1.5 mmol) were weighted in a flask and were then dissolved in a mixed solvent (8: 3 v/v, 11 mL) of dichloromethane and methanol. BnMe₃N⁺ICl₂⁻ (418 mg, 1.2 mmol) was added to this solution, and stirring was performed for 3 hours at room temperature. After an insoluble substance was removed by filtration, a saturated aqueous solution (20 mL) of sodium hydrogen sulfite was added to the filtrate, and the mixture was extracted with diethyl ether (20 mL×3). After organic layers were collected and dried by anhydrous sodium sulfate, condensation under reduced pressure was performed. Purification of an obtained crude product by a column chromatography (silica gel, hexane-ethyl acetate from 1:0 to 40:1) gave the N,N-diarylamine having an iodine atom at the para-position. The structure of the N,N-diarylamine having an iodine atom at the para-position was analyzed by $^1$H NMR (CDCl$_3$), $^{13}$C NMR (CDCl$_3$), and a high-resolution mass spectroscopy (HRMS, FAB). The data thereof are shown below.

$^1$H NMR (CDCl$_3$) δ 0.97 (d, J=7.0 Hz, 12H), 1.06 (d, J=7.0 Hz, 6H), 2.62 (septet, J=7.0 Hz, 1H), 2.92 (septet, J=7.0 Hz, 2H), 5.31 (s, 1H), 6.49 (s, 2H), 7.09-7.20 (m, 10H), 7.36 (s, 2H); $^{13}$C NMR (CDCl$_3$) δ 22.9 (4C), 24.1 (2C), 28.4 (2C), 34.2, 77.8, 120.3 (2C), 127.0 (2C), 127.9 (4C), 129.0 (4C), 130.8 (2C), 134.1 (2C), 138.6 (2C), 138.9 (2C), 140.9, 144.1, 146.1; HRMS (FAB) calcd for C$_{33}$H$_{37}$IN[M+H]$^+$ 574.1971. found 574.1989

By the use of the N,N-diarylamine having an iodine atom at the para-position thus obtained (0.1 mmol, 5 mol %), a corresponding ammonium pyrosulfate (catalyst shown above the arrow located at a lower stage of the formula (7)) was produced by the same method as that of the "first production method (1)" of Example 1, and the product thus obtained was immediately and directly used for a hydrolysis reaction of methyl laurate. The reaction conditions were as shown in the formula (7), and the yield was 87%.

This application claims the benefit of Japanese Patent Application No. 2011-289040, filed Dec. 28, 2011, which is hereby incorporated by reference herein in its entirety.

Industrial Applicability

The present invention can be primarily applied to a medical chemistry industry and can be used for production of various types of carboxylic acids and alcohols which are used, for example, as various types of medicines and organic materials. In particular, the present invention is useful in the fields relating to oils and fats (process for producing aliphatic carboxylic acids from oils and fats), plasticizers (process for recovering alcohol components from residues left in ester distillation stills), optically active intermediates (process for producing high-purity optically active carboxylic acids), and the like.

The invention claimed is:

1. A method for producing a carboxylic acid and an alcohol, the method comprising:
producing a carboxylic acid and an alcohol by hydrolyzing a carboxylic acid ester in water in the presence of an ammonium pyrosulfate catalyst represented by the following general formula (1):

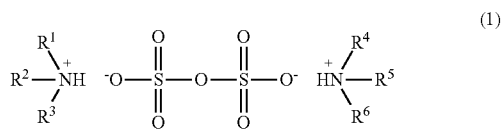

(1)

wherein, R$^1$ and R$^4$ each independently represent an aryl group, and R$^2$, R$^3$, R$^5$, and R$^6$ each independently represent an aryl group, an alkyl group, an alkenyl group, an alkynyl group, a cycloalkyl group, or a hydrogen atom.

2. The method for producing a carboxylic acid and an alcohol according to claim 1,
wherein the ammonium pyrosulfate catalyst is an ammonium pyrosulfate catalyst represented by the following general formula (2):

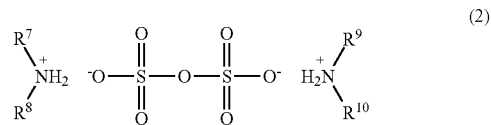

(2)

which, R$^7$, R$^8$, R$^9$, and R$^{10}$ each independently represent an aryl group.

3. The method for producing a carboxylic acid and an alcohol according to claim 1,
wherein the carboxylic acid ester is an optically active carboxylic acid ester, and the carboxylic acid and/or the alcohol is an optically active carboxylic acid and/or an optically active alcohol.

4. The method for producing a carboxylic acid and an alcohol according to claim 1,
wherein one of the alcohol and the carboxylic acid is water soluble.

* * * * *